United States Patent [19]

Astegger et al.

[11] Patent Number: 5,409,532
[45] Date of Patent: Apr. 25, 1995

[54] AMINE-OXIDES

[75] Inventors: Stephan Astegger; Dieter Eichinger, both of Vöcklabruck; Heinz Falk, Linz; Günter Teubl, Schörfling, all of Austria

[73] Assignee: Lenzing Aktiengesellschaft, Austria

[21] Appl. No.: 7,167

[22] Filed: Jan. 21, 1993

[30] Foreign Application Priority Data

Jan. 23, 1992 [AT] Austria ................... 109/92

[51] Int. Cl.⁶ .................... C08L 1/00; C08L 1/02
[52] U.S. Cl. .................. 106/163.1; 106/164; 106/165; 106/166; 106/168; 106/186; 564/297
[58] Field of Search ............ 564/297; 106/163.1, 106/168, 164, 165, 166, 186

[56] References Cited

U.S. PATENT DOCUMENTS

| | | | |
|---|---|---|---|
| 2,179,181 | 11/1939 | Graenacher et al. | 106/40 |
| 3,317,430 | 5/1967 | Priestley et al. | 564/297 |
| 3,447,939 | 6/1969 | Johnson | 106/135 |
| 3,447,956 | 6/1969 | Johnson | 117/154 |
| 3,449,430 | 6/1969 | Dohr et al. | 564/297 |
| 3,449,431 | 6/1969 | Swenson | 260/584 |
| 3,449,432 | 6/1969 | Bortslap et al. | 260/584 |
| 3,508,941 | 4/1970 | Johnson | 106/125 |
| 4,145,532 | 3/1979 | Franks et al. | 536/56 |
| 4,196,282 | 4/1980 | Franks et al. | 536/56 |
| 4,256,613 | 3/1981 | Franks et al. | 260/13 |
| 4,284,545 | 8/1981 | Franks et al. | 260/29.6 |
| 5,043,075 | 8/1991 | Dietmar et al. | 210/664 |
| 5,053,138 | 10/1991 | Korger et al. | 210/670 |
| 5,094,690 | 3/1992 | Zikeli et al. | 106/198 |
| 5,118,423 | 6/1992 | Astegger et al. | 210/638 |

FOREIGN PATENT DOCUMENTS

| | | |
|---|---|---|
| 393841 | 12/1991 | Austria . |
| 047929 | 3/1982 | European Pat. Off. . |
| 0075261 | 3/1983 | European Pat. Off. . |
| 356419 | 2/1990 | European Pat. Off. . |
| 393908 | 10/1990 | European Pat. Off. . |
| 402347 | 12/1990 | European Pat. Off. . |
| 427701 | 5/1991 | European Pat. Off. . |
| 448924 | 10/1991 | European Pat. Off. . |
| 2848471 | 6/1979 | Germany . |
| 218104 | 1/1985 | Germany . |
| 229708 | 11/1985 | Germany . |
| 59-167558 | 9/1984 | Japan . |
| 8304415 | 12/1983 | WIPO . |

Primary Examiner—Peter O'Sullivan
Attorney, Agent, or Firm—Brumbaugh, Graves, Donohue & Raymond

[57] ABSTRACT

Amine-oxides of the general formula:

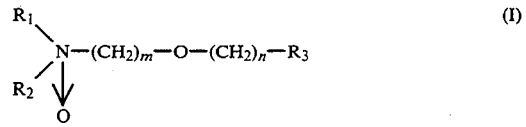

wherein $R_1$ and $R_2$ are alkyl groups with 1 to 4 C-atoms, $R_3$ is hydrogen, a hydroxyl group or an alkoxy group with 1 to 4 C-atoms and m and n are whole numbers which fulfil the conditions $1 \leq m \leq 8$ and $0 \leq n \leq 4$ respectively, with the proviso that n is not 0 if $R_3$ is a hydroxyl group or an alkoxy group, can be used with advantage for the preparation of mouldable or spinnable cellulose solutions which have a reduced tendency to crystallise.

11 Claims, No Drawings

AMINE-OXIDES

The invention concerns tertiary amine-oxides which can be used for the preparation of mouldable or spinnable cellulose solutions.

It is known from U.S. Pat. No. 2,179,181 that tertiary amine-oxides enable cellulose to dissolve without having to make derivatives and that cellulose mouldings such as fibres can be made by precipitation from these solutions. Further processes for the preparation of cellulose solutions are described in U.S. Pat. No. 3,447,939, U.S. Pat. No. 3,447,956 and U.S. Pat. No. 3,508,941, wherein cyclic amine-oxides are preferably used as the solvent.

According to U.S. Pat. No. 4,196,282 however, the cited processes have the disadvantage that they only enable the preparation of relatively dilute solutions with a maximum cellulose content of 10 weight %. According to the U.S. Pat. No. 4,196,282 cited above, higher concentrations of cellulose can only be achieved if amine-oxide containing water is used or if additional water is added to the amine-oxide/cellulose mixture. It is proposed that up to 29 wt % water be used in the mixture. The disadvantage of this however is that the volumes containing amine-oxide, which occur after the precipitation stage and which must be worked up, become very large.

With the solvent which is mostly used nowadays, N-methyl-morpholine-N-oxide (NMMO), water or another non-solvent which is miscible with NMMO must be added to the cellulose-NMMO suspension since NMMO occurs in the solid state at room temperature. For this reason the cellulose solution which is obtained has a strong tendency to crystallise which is also a disadvantage.

The invention seeks to avoid these disadvantages and to solve the problem of making available tertiary amine-oxides which allow the preparation of mouldable or spinnable cellulose solutions with the lowest possible tendency to crystallise. A further problem consists of making available cellulose solutions with the lowest possible water content and with a cellulose content of greater than 10 wt % based on the weight of the solution.

The tertiary amine-oxides used according to the invention have the general formula:

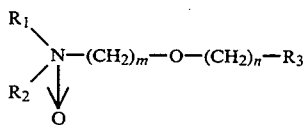
(I)

where:

$R_1$ and $R_2$ are alkyl groups with 1 to 4 C-atoms, $R_3$ is hydrogen, an hydroxyl group or an alkoxy group with 1 to 4 C-atoms, m and n are whole numbers which fulfil the conditions $1 \leq m \leq 8$ or $0 \leq n \leq 4$ respectively, with the proviso that n is not 0 if $R_3$ is a hydroxyl group or an alkoxy group.

These compounds are new insofar as $R_3$ is not an alkoxy group.

Amine-oxides of the general formula (I) given above have proved to be especially suitable when m is the number 2 and n is one of the numbers 0, 1 or 2.

2-(N,N-dimethylaminoethoxy)-ethanol-N-oxide with the formula:

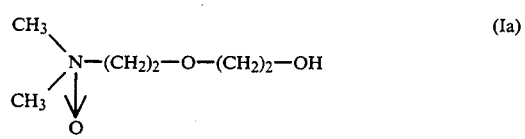
(Ia)

has proved to be an excellent solvent, This is most surprising since a compound which is very similar In structure is described In U.S. Pat. No. 4,196,282 as a poor solvent for cellulose, This compound is 2-(2-hydroxy-propoxy)-N-ethyl-N,N-dimethylamine-N-oxide which can only dissolve up to 7.5 wt % of cellulose (based on the solution) and only then if between 5 and 10 wt % of water is present in the solution (see Table in column 6 of the U.S. Pat. No. 4,196,282). In contrast, the amine-oxides used according to the invention allow the preparation of cellulose solutions which are practically free from water and which have a cellulose content of above 10 wt % (based on the solution). Naturally the solution according to the invention can contain water or another non-solvent (for cellulose) as an auxiliary material.

The compounds according to the invention can be prepared by the oxidation of corresponding tertiary amines of the general formula (II) known per se:

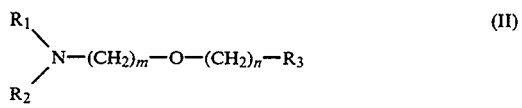
(II)

where:

$R_1$, $R_2$, $R_3$, m and n have the meanings given above.

The conversion of tertiary amines into their N-oxides is generally known and can be carried out, for example, by treatment with $H_2O_2$.

The amine-oxides according to the invention are substantially cheaper to prepare than the N-methyl-morpholine-N-oxide (NMMO) which is so widely used nowadays, since the corresponding starting amine is manufactured on a larger scale than is morpholine or methylmorpholine. Furthermore the amine-oxides used according to the invention are substantially more readily biodegradable (determined according the Zahn-Welles test) than cyclic amine-oxides.

It has been shown that the amine-oxides according to the invention enable cellulose to dissolve readily. The cellulose solutions according to the invention have substantially less tendency to crystallise than NMMO solutions. A preferred embodiment of the cellulose solution according to the invention, which is mouldable and spinnable, contains above 10 wt % cellulose and is water-free.

It has also been shown that even mixtures of the amine-oxides according to the invention and NMMO can be used to prepare cellulose solutions which are still mouldable and can still be shaped at room temperature as long as the amount of NMMO is less than 70 wt % (based on the amine-oxide mixture).

The solution according to the invention can additionally also contain a stabiliser. Compounds of the flavone group, such as rutin (3,3',4',5,7-pentahydroxy-flavone-3-rutinocide), quercetin (3',3,4',5,7-pentahydroxy-flavone) or morin (2',3,4',5,7-pentahydroxy-flavone), preferably in amounts from 0.001 to 1.5 wt % based on the moulding material or spinning material, have proved to be especially suitable. These stabilisers are known from AT-B 393 841. The stabilisers described in EP-A-0 111 518, EP-A-0 047 929, DD-A 218 104 and DD-A 229 708 can also be used with success.

A mixture of $H_2O_2$ and oxalic acid can also be used as a stabiliser. It has been shown that the discolouration, which usually occurs during the preparation of the solution and on warming, is reduced if 0.01 to 1%, preferably 0.1%; of $H_2O_2$ and 0.03 to 2%, preferably 0.1%; of a stabiliser for $H_2O_2$, preferably oxalic acid, is present in the solution.

The solution according to the invention can be prepared by mixing and warming an amine-oxide according to the invention, optionally together with NMMO, with disintegrated cellulose and optionally with another soluble polymer, whereby any water which is possibly present is optionally removed. Polyamides, cellulose acetate or polyesters are examples of other suitable polymers.

The amine-oxides used according to the invention can even be used with a water content of about 50 wt % for the preparation of cellulose solutions. In this case the procedure for making the cellulose solution described in EP-A-0 356 419 has proved to be especially worthwhile. In cases where the water content is low or where there is no water, it is possible to prepare the cellulose solution in an extruder, in a barrel mixer or the like, In a stirred vessel or in a pan mixer.

Cellulose mouldings are preferably prepared in such a way that the solution according to the invention, which is mouldable or spinnable, is pressed through a shaping device and optionally is stretched and coagulated. It has been shown that the solution according to the Invention can be processed according to all known procedures such as wet spinning and dry/wet spinning ("air-gap spinning") and can be used to make films.

The dissolved amine-oxides according to the invention can be separated and recovered from the precipitation bath in a simple way, wherein the solutions to be purified are brought into contact with an anionic exchanger and the purified solutions are separated from the anionic exchanger, wherein the purification is carried out in a one-stage process with an anionic exchanger in which the functional group consists exclusively of quaternary tetraalkyl-ammonium groups of the formula:

$$-CH_2-N^+(CH_3)_3 X^- \text{ or}$$
$$-CH_2-N^+[(CH_3)_2(CH_2OH)]X^-$$

where $X^-$ is the anion of an inorganic acid or organic acid, whereupon the anionic exchanger is regenerated with an aqueous solution of acid.

It is advantageous to use an anionic exchanger in which the anion $X^-$ is derived from a volatile acid particularly carbonic acid, formic acid or acetic acid. Regeneration of the anionic exchanger can be carried out with an aqueous solution of formic acid, acetic acid or carbonic acid and this solution can further contain up to 5 wt % of a hydroxy-carboxylic acid, especially tartaric acid. A purification process of this type for spinning bath solutions is known from EP-A-0 427 701 for the separation of NMMO.

The amine-oxides used according to the invention can also be separated according to the process described in EP-A-0 402 347. in this process the used precipitation bath is brought into contact with a cationic exchange resin in order to charge the cationic exchanger with the amine-oxides, whereupon the charged cationic exchanger is washed and the amine-oxide is eluted, wherein a cationic exchange resin is used in which the anchor groups consist of carboxyl groups and wherein the cationic exchanger charged with the amine-oxides is treated with an aqueous solution of a weak acid with a $pK_a$ value of greater than 3.0 in order to elute the amine-oxides.

In order to purify the aqueous solutions of amine-oxides, particularly spinning bath solutions, the solutions can also be brought into contact with adsorbents and then subjected to filtration. Aluminium oxide, silicon oxide or charcoal are preferably used as adsorbents. The adsorbents desirably have a particle size of less than 0.15 min. The presence of adsorbent facilitates the filtration of any fine suspended matter which may be present.

In order to obtain a concentrated solution of the amine-oxides according to the invention, or their amines, it is also possible to separate water from the used spinning bath wherein the spinning bath solution is forced through a semipermeable membrane in a reverse osmosis plant at a pressure which is greater than the osmotic pressure. Such a process is described for NMMO solutions in EP-A-0 448 924.

The Austrian patent application No. A 109/92 on which the priority of the present application is based, is hereby incorporated by reference.

The invention is explained in yet more detail with the following Examples, wherein Example 1 relates to the synthesis of 2-(N,N-dimethylaminoethoxy)-ethanol-N-oxide and other tertiary amine-oxides whilst Examples 2 to 10 concern the preparation of cellulose solutions and in part their further processing.

Cellulose solutions with a cellulose content of over 10 wt % (based on the solution), which were practically water-free and which had an extremely low tendency to crystallise, were prepared with all the N-oxides cited in Example 1.

EXAMPLE 1

A total of 802 g aqueous $H_2O_2$ (30%; concentration determined by redox titration with $KMnO_4$) containing 240.6 g (=7.08 mol) $H_2O_2$ is added in several aliquots to 788 g (=5.9 mol) 2-(N,N-dimethylaminoethoxy)-ethanol in such a way that the temperature of the reaction solution does not rise above 30° C.; the reaction vessel is cooled in a glycol bath (temperature <0° C.) as necessary. During the course of the oxidation, a total of 70 ml water is added to dilute the reactants. After completion of the $H_2O_2$ addition, the reaction mixture is allowed to warm up to room temperature. The reaction mixture is stirred overnight, then warmed to ca. 70° C. and held at this temperature for about 3 hours. A catalase solution (ca. 1%) is then added to destroy the excess $H_2O_2$, wherein the addition is repeated until foam is no longer developed. The solution obtained in this way is water-clear and has an amine-oxide concentration of ca. 50%.

To isolate the amine-oxide from the solution which is obtained, water is first separated by azeotropic distillation with benzene. The amine-oxide is then separated from the benzene phase and the remaining residues of benzene are removed by rotary evaporation. Crystals are obtained which are recrystallised from dry acetone and dried in vacuo.

The amine-oxide has the following physical properties:

| IR Spectrum: | | | |
|---|---|---|---|
| Wave Number | Type | Oscillation | Group |
| 2865 | singlet | —CH— str. | —O—CH$_2$— |
| 1471 | | —CH$_3$ def. asym. | |
| 1456 | doublet | —CH$_2$— def. | |
| 1609 | singlet | —N— def. | —CH$_2$—N— |
| 1397 | singlet | —CH$_3$ def. sym. | —N(CH$_3$)$_2$ |
| 1127 | singlet | —C—O—C str. asym. | —CH$_2$—O—CH$_2$— |
| 1076 | singlet | —C—O— str. | —CH$_2$—OH |
| 958 | singlet | —N—O— str. | —N—O— |

(def. = deformation oscillation; str. = stretching oscillation; sym. = symmetrical; asym. = asymmetrical)

The 46,9% and 96% aqueous solutions of the amine-oxide obtained had refractive indices (measured by daylight) of 1,4100 and 1,4830 respectively (at 20° C.) from which the refractive index for the amine-oxide itself is calculated to be 1.4889.

Further amine-oxides were prepared from the corresponding tertiary amines according to the above procedures and characterised by means of $^1$H-NMR spectroscopy. This data is summarised in the following Table.

| N-Oxide | $^1$H-NMR, CDCl$_3$, 200 MHz $\delta$ [ppm] |
|---|---|
| 2-(N,N-Dimethyl- amino)-ethanol-N- Oxide | 4,10 (2H, t, J=4, 83 Hz, —N—CH$_2$CH$_2$—OH) 3,44 (2H, t, J=4, 83 Hz, —N—CH$_2$—CH$_2$—OH) 3,28 (6H, s, —, (CH$_3$)$_2$—N—) |
| 2-Methoxy-1-N,N- dimethyl-ethyl- amine-N-Oxide | 3,77 (2H, t, J=4, 54 Hz, —N—CH$_2$—CH$_2$—O—) 3,30 (2H, t, J=4, 53 Hz, —N—CH$_2$—CH$_2$—O—) 3,22 (3H, s, —, —O—CH$_3$) 3,07 (3H, s, —, —(CH$_3$)$_2$—N—) |
| 2-Ethoxy-1-N,N- dimethyl-ethyl- amine-N-Oxide | 3,98 (2H, t, J=4, 59 Hz, —N—CH$_2$—CH$_2$—O—) 3,55 (2H, q, J=6, 99 Hz, CH$_3$—CH$_2$—O—) 3,44 (2H, t, J=4, 59 Hz, —N—CH$_2$—CH$_2$—O—) 3,25 (6H, s, —, (CH$_3$)$_2$—N—) 1,20 (3H, t, J=6, 99 Hz, CH$_3$—CH$_2$—O—) |
| N,N-Dimethyl- amino-diglycol-N- Oxide | 4,05 (2H, t, J=4, 48 Hz, —N—CH$_2$—CH$_2$—O—) 3,68 (2H, t, J=4, 97 Hz, —N—CH$_2$—CH$_2$—O—) 3,58 (2H, t, J=4, 95 Hz, —O—CH$_2$—CH$_2$—OH) 3,43 (2H, t, J=4, 59 Hz, —O—CH$_2$—CH$_2$—OH) |
| N,N-Dimethyl- amino-3,6-dioxo- triethylen-N-Oxide | 3,87 (2H, t, J=4, 42 Hz, —N—CH$_2$—CH$_2$—O—) 3,40 (8H, m, —N—(CH$_2$)$_2$—O—(CH$_2$)$_2$—O—CH$_2$—CH$_3$) 3,08 (6H, s, —, (CH$_3$)$_2$—N—) 1,03 (3H, t, J=7, 00 Hz, CH$_3$—CH$_2$—O—) |
| 3-Methoxy-N,N- dimethyl-N-propyl- amine-N-Oxide | 3,30 (2H, t, J=5, 72 Hz, —CH$_2$—CH$_2$—O—CH$_2$—CH$_3$) 3,16 (2H, t, J=3, 57 Hz, —N—CH$_2$—CH$_3$) 3,12 (3H, s, —, CH$_3$—O—CH$_2$—) 3,00 (6H, s, —, (CH$_3$)$_2$—N—) 2,01 (2H, m, —, —N—CH$_2$—CH$_2$—CH$_2$—O—) |
| 3-Ethoxy-N,N- dimethyl-N-propyl- amine-N-Oxide | 3,35 (2H, t, J=5, 47 Hz, —N—CH$_2$—CH$_2$—CH$_2$—O—) 3,30 (2H, t, J=7, 00 Hz, —O—CH$_2$—CH$_3$) 3,22 (2H, t, J=5, 42 Hz, —N—CH$_2$—CH$_2$—CH$_2$—O—) 3,03 (6H, s, —, (CH$_3$)$_2$—N—) 2,02 (2H, m, —, —N—CH$_2$—CH$_2$—CH$_2$—O—) 1,00 (3H, t, J=7, 00 Hz, —O—CH$_2$—CH$_3$) |

EXAMPLE 2

167 g 2-(N,N-dimethylaminoethoxy)-ethanol-N-oxide (content 96%) is mixed with 43 g cellulose (Buckeye V5; moisture: 7%) to give a suspension and 0.08 g rutin is added as a stabiliser. Then 10 g water is distilled off under vacuum in a kneader. A clear brown-coloured cellulose solution is obtained with a cellulose concentration of 20% and an amine-oxide concentration of 80%.

EXAMPLE 3

177.1 g 2-(N,N-dimethylaminoethoxy)-ethanol-N-oxide (water content 4%) is mixed with 37.3 g cellulose (Buckeye V5; dry content 93%) and 0.08 g rutin is added as a stabiliser. Then 9 g water is distilled off under vacuum in a kneader. A clear brown-coloured cellulose solution is obtained with a cellulose concentration of 16.9% and an amine-oxide concentration of 82.8%. The water content amounts to 0.4%

EXAMPLE 4

135 g 2-(N,N-dimethylaminoethoxy)-ethanol-N-oxide (content 96%) is mixed in a kneader with 15 g cellulose (Buckeye V5; moisture 7%), then 0.08 g rutin is added as a stabiliser and 7 g water is distilled off under vacuum. A clear brown-coloured solution is obtained with a cellulose concentration of 10% and an amine-oxide concentration of 90%. Cellulose fibres with the following properties were spun from this solution:

| Titre: | 2.72 dtex |
|---|---|
| Strength (conditioned): | 36 cN/tex |
| Elongation (conditioned): | 8.5% |
| Loop strength: | 17 cN/tex |
| Loop elongation: | 2.7% |

Cellulose precipitated in a water bath has a degree of polymerisation (DP) of 500 (Cuen method).

EXAMPLE 5

317.7 g 2-(N,N-dimethylaminoethoxy)-ethanol-N-oxide (water content 53.1%) is mixed with 16.1 g cellulose (Buckeye V5; dry content 93%) and 0.08 g rutin is added as a stabiliser. Then 159.7 g water is distilled off under vacuum in a kneader. A clear brown-coloured cellulose solution is obtained containing 9.4% cellulose, 85.6% amine-oxide and 5.0% water. The cellulose precipitated into water has a DP of 510.

EXAMPLE 6

18 g cellulose (Buckeye V5; dry content 93%) is mixed with 69 g 2-(N,N-dimethylaminoethoxy)-ethanol-N-oxide (content 90%) and 117.2 g NMMO (content 59.7%), and 0.06 g rutin is added as a stabiliser. 44 g water is then distilled off in a kneader. A clear brown cellulose solution is obtained containing 11.7% cellulose and 88.8% N-oxide. The cellulose precipitated into water has a DP of 570.

EXAMPLE 7

198 g 2-(N,N-dimethylaminoethoxy)-ethanol-N-oxide (water content 21.2%) is mixed with 25.8 g BKZ (sulphite cellulose; dry content 93%) and 0.1 g propyl gallate is added as a stabiliser. Then ca. 15 g water is distilled off in a kneader. 20 g N-methyl-morpholine-N-oxide-monohydrate is added after 1 hour and kneading is continued until a clear solution is obtained. The solution contains 11% cellulose, 80% amine-oxides and 9.3% water.

Cellulose fibres with the following properties were spun from this solution:

| Titre: | 1.60 dtex |
|---|---|
| Strength (conditioned): | 38 cN/tex |
| Elongation (conditioned): | 8.8% |
| Loop strength: | 18.2 cN/tex |
| Loop elongation: | 2.4% |

EXAMPLE 8

198 g 2-(N,N-dimethylaminoethoxy)-ethanol-N-oxide (water content 21.2%) is mixed with 25.8 g BKZ (sulphite cellulose; dry content 93%) and 0.2 g oxalic acid/hydrogen peroxide mixture is added as a stabiliser. Then ca. 15 g water is distilled off in a kneader. 20 g N-methyl-morpholine-N-oxide-monohydrate is added after 1 hour and kneading is continued until a clear solution is obtained.

EXAMPLE 9

196 g 2-(N,N-dimethylaminoethoxy)-ethanol-N-oxide (water content 21.2%) is mixed with 25.8 g Viscokraft LV (sulphate cellulose; dry content 93%), 2 g polyvinyl acetate as an additional polymer component and 0.1 g hydroxyethylidene-1,1-diphosphonic acid as a stabiliser. Then ca. 40 g water is distilled off in a kneader. 20 g N-methyl-morpholine-N-oxide-monohydrate is added after 1 hour and kneading is continued until a clear solution is obtained. The solution contains 11.8% cellulose, 1% polyvinyl acetate, 84.6% amine-oxides and 2.5% water.

EXAMPLE 10

174 g 2-(N,N-dimethylaminoethoxy)-ethanol-N-oxide (water content 11.2%) is mixed with 24.0 g Viscokraft LV (sulphate cellulose; dry content 93%), 2 g polyvinyl alcohol as an additional polymer component and 0.1 g rutin as a stabiliser. Then ca. 21 g water is distilled off in a kneader. Then 20 g N-methyl-morpholine-N-oxide-monohydrate is added after 1 hour and kneading is continued until a clear solution is obtained. The solution contains 11% cellulose, 1% polyvinyl alcohol, 84.3% amine-oxides and 3.7% water.

Cellulose fibres with the following properties were spun from this solution:

| Titre: | 1.36 dtex |
|---|---|
| Strength (conditioned): | 28.8 cN/tex |
| Elongation (conditioned): | 10.2% |
| Loop strength: | 12.8 cN/tex |
| Loop elongation: | 2.2% |

What we claim is:

1. A solution which can be molded or spun, said solution comprising cellulose and tertiary amine-oxides of the general formula:

$$\begin{array}{c} R_1 \\ \phantom{R}\diagdown \\ \phantom{RR}N\text{---}(CH_2)_m\text{---}O\text{---}(CH_2)_n\text{---}R_3 \\ \phantom{RR}\diagup \phantom{X}\downarrow \\ R_2 \phantom{XXX} O \end{array} \qquad (I)$$

wherein each of $R_1$ and $R_2$ is an alkyl group with 1 to 4 C-atoms, $R_3$ is selected from the group consisting of a hydrogen atom, a hydroxyl group and an alkoxy group with 1–4 C-atoms, and m and n are whole numbers which fulfill the conditions $1 \leq m \leq 8$ and $1 \leq n \leq 4$ respectively.

2. Solution in accordance with claim 1, wherein the tertiary amine-oxide is 2-(N,N-dimethylaminoethoxy)-ethanol-N-oxide of the formula:

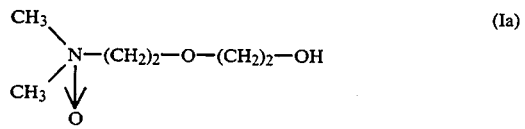

3. Solution in accordance with claim 1, wherein an auxiliary material such as water or a non-solvent is also present.

4. Solution in accordance with claim 1, said solution being free from water and containing above 10 wt % cellulose.

5. Solution in accordance with claim 1, further comprising a stabiliser.

6. Solution in accordance with claim 5, wherein the stabiliser is a compound of the flavone group.

7. Solution in accordance with claim 6, wherein the compound of the flavone group is rutin (3,3',4',5,7-pentahydroxy-flavone-3-rutinocide), quercetin (3',4,4',5,7-pentahydroxy-flavone), or morin (2',3,4',5,7-pentahydroxy-flavone).

8. Solution in accordance with claim 6, wherein the amount of the compound of the flavone group is from 0.001 to 1.5 wt %, based on the moulding material or spinning material.

9. Solution in accordance with claim 6, wherein the stabiliser is a mixture of $H_2O_2$ and oxalic acid.

10. Solution in accordance with claim 1, further comprising another polymer as well as cellulose.

11. Solution in accordance with claim 1, further comprising N-methyl-morpholine-N-oxide as an additional amine-oxide.

* * * * *

UNITED STATES PATENT AND TRADEMARK OFFICE
CERTIFICATE OF CORRECTION

PATENT NO. : 5,409,532

DATED : April 25, 1995

INVENTOR(S) : Astegger et al.

It is certified that error appears in the above-indentified patent and that said Letters Patent is hereby corrected as shown below:

Col. 2, line 11, "In" should read --in--

Col. 2, line 12, "In" should read --in--

Col. 3, line 10, "0.1%;" should read --0.1%--

Col. 3, line 11, "0.1%;" should read --0.1%--

Col. 3, line 29, "In" should read --in--

Col. 3, line 66, "in this" read --In this--

Col. 5, line 15, "46,9%" should read --46.9%--

Col. 5, line 17, "1,4100 and 1,4830" should read --1.4100 and 1.4830--

Col. 8, line 49, "3',4,4',5,7-" should read --3',3,4',5,7- --

Col. 8, line 56, "claim 6" should read --claim 5--

Signed and Sealed this

Fourth Day of July, 1995

Attest:

BRUCE LEHMAN

*Attesting Officer*     *Commissioner of Patents and Trademarks*